United States Patent
Chen et al.

(10) Patent No.: US 11,708,321 B2
(45) Date of Patent: Jul. 25, 2023

(54) METHOD FOR PREPARING (DIMETHYLAMINOMETHYLENE) MALONONITRILE USING A MICRO REACTION SYSTEM

(71) Applicant: Fudan University, Shanghai (CN)

(72) Inventors: Fener Chen, Shanghai (CN); Dang Cheng, Shanghai (CN); Meifen Jiang, Shanghai (CN); Minjie Liu, Shanghai (CN); Huashan Huang, Shanghai (CN); Lulu Wang, Shanghai (CN)

(73) Assignee: Fudan University, Shanghai (CN)

( * ) Notice: Subject to any disclaimer, the term of this patent is extended or adjusted under 35 U.S.C. 154(b) by 429 days.

(21) Appl. No.: 17/103,520

(22) Filed: Nov. 24, 2020

(65) Prior Publication Data

US 2022/0089524 A1    Mar. 24, 2022

(30) Foreign Application Priority Data

Sep. 18, 2020    (CN) .......................... 202010987170.9

(51) Int. Cl.
*C07C 253/20* (2006.01)
*B01J 19/00* (2006.01)
*C07C 255/25* (2006.01)

(52) U.S. Cl.
CPC ......... *C07C 253/20* (2013.01); *B01J 19/0093* (2013.01); *B01J 2219/00797* (2013.01); *B01J 2219/00867* (2013.01); *B01J 2219/00891* (2013.01); *B01J 2219/00997* (2013.01); *C07C 255/25* (2013.01)

(58) Field of Classification Search
None
See application file for complete search history.

(56) References Cited

FOREIGN PATENT DOCUMENTS

| CN | 103261173 B | 9/2015 |
| IN | 4773/DELNP/2013 A | 11/2014 |
| WO | 2012075677 A1 | 6/2012 |

OTHER PUBLICATIONS

Lei Zhao,Xiao-Dong Ma,and Fen-Er Chen;Development of Two Scalable Syntheses of 4-Amino-5-aminomethyl-2-methylpyrimidine: Key Intermediate for Vitamin B1;Organic Process Research & Development, 2012, 16, 57-60.
Kenji Ikawa, Fumitaka Takami,Yutaka Fukui and Kanji Tokuyama;A Novel Reagent for the Vilsmeier-Haack Reaction;Tetrahedron Letters, 1969, 38, 3279-3281.
E.Nicholas Gate,Michael D.Threadgill,Malcolm F.G.Stevens,David Chubb,Lisa M.Vickers,Simon P.Langdon,John A. Hickman,and Andreas Gescher;Structural studies on bioactive compounds. 4.1 A structure-antitumor activity study on analogs of N-methylformamide;Journal of Medicinal Chemistry, 1986, 29, 1046-1052.
Rajni Kant,Vivek K. Gupta,Kamini Kapoor,D. R. Patil and Madhukar B. Deshmukh;2-[(Dimethylamino)methylidene]-propanedinitrile;Acta Crystlliographica Section E, 2013, E69, o433.
Veera Reddy. Arava , Laxminarasimhulu. Gorentla, Sreenivasula Reddy. Bandatmakuru and Udaya Bhaskara Rao Siripalli;New reagents from "N, N-Dimethyl amino methoxy methylenium methyl sulphate"—Synthesis of 3-Amino-4-cyano pyrazole;Der Pharma Chemica, 2010, 2, 178-186.

*Primary Examiner* — Joseph R Kosack (57) ABSTRACT

A method for preparing (dimethylaminomethylene) malononitrile by using a micro reaction system. Cyanoacetamide, N,N-dimethylformamide and a catalyst are mixed to obtain a mixture, and the mixture and phosphorus oxychloride are simultaneously pumped into the micro reaction system that includes a micromixer and a microchannel reactor connected in series for continuous dehydration condensation. After adjusted to a target pH, the crude product is subjected to continuous liquid-liquid extraction with an organic solvent in a centrifugal extraction unit comprising a plurality of annular centrifugal extractors connected in series. The organic phase is collected to obtain the target product (dimethyl aminomethylene) malononitrile.

20 Claims, 2 Drawing Sheets

METHOD FOR PREPARING (DIMETHYLAMINOMETHYLENE) MALONONITRILE USING A MICRO REACTION SYSTEM

CROSS-REFERENCE TO RELATED APPLICATIONS

This application claims the benefit of priority from Chinese Patent Application No. 202010987170.9, filed on Sep. 18, 2020. The content of the aforementioned application, including any intervening amendments thereto, is incorporated herein by reference in its entirety.

TECHNICAL FIELD

The present disclosure relates to organic synthesis, in particular to a method for preparing (dimethylaminomethylene) malononitrile using a micro reaction system.

BACKGROUND (Dimethylaminomethylene) malononitrile (I), of which the chemical structure is shown in formula (I), is a key intermediate in the synthesis of Vitamin Bi.

(I)

Singh et al. (*Indian Journal of Chemistry, Section B: Organic Chemistry Including Medicinal Chemistry*, 1984, 23B, 1176-1180) reported a method for preparing the (dimethylaminomethylene) malononitrile (I) through reacting N,N-dimethyl-N-(methyl sulfanylmethylene) ammonium iodide with malononitrile. However, the reactant N,N-dimethyl-N-(methyl sulfanylmethylene) ammonium iodide was expensive and difficult to prepare. Ikawa et al. (*Tetrahedron Letters*, 1969, 38, 3279-3281) developed another process for preparing the (dimethylaminomethylene) malononitrile (I), in which malononitrile, N,N-dimethylformamide and ethyl chloroformate were used as reactants. This method was seriously limited by the extremely low yield (only 10%). Gate et al. (*Journal of Medicinal Chemistry*, 1986, 29, 1046-1052) proposed a preparation of the (dimethylaminomethylene) malononitrile (I) from N,N-dimethylformamide diethyl acetal and malononitrile, but the yield was still unsatisfactory (21%). In the method designed by Kant et al. (*Acta Crystlhographica Section E*, 2013, E69, o433), N,N-dimethylformamide dimethyl acetal was reacted with malononitrile to produce the (dimethylaminomethylene) malononitrile (I), and this method increased the yield to 75%. However, N,N-dimethylformamide dimethyl acetal has high price and high production cost. It has been published by Arava et al. (*Der Pharma Chemica*, 2010, 2, 178-186) that dimethyl sulfate first reacted with N,N-dimethylformamide to form a methyl sulfate salt, which further reacted with malononitrile in the presence of triethylamine to prepare the (dimethylaminomethylene) malononitrile (I). However, the dimethyl sulfate used in this method was highly toxic. The above-mentioned methods all use expensive malononitrile as reactant, thereby increasing the production cost of the (dimethylaminomethylene) malononitrile (I). Chinese patent No.103261173B, Indian patent IN4773/DELNP/2013, international patent WO 2012/075677 and Chen Fener et al. (*Organic Process Research & Development*, 2012, 16, 57-60) all disclosed a one-pot preparation of the (dimethylaminomethylene) malononitrile (I), in which cyanoacetamide, N,N-dimethylformamide and phosphorus oxychloride were reacted in the presence of pyridine at a low temperature. Unfortunately, this process is both time- and energy-consuming, and has relatively low yield (40%-70%). The above-mentioned methods were all carried out in a traditional batch reactor. There is an urgent need for those skilled in the art to develop a method for preparing (dimethylaminomethylene) malononitrile (I) with less time consumption, high yield, low preparation cost, low energy consumption and high process efficiency.

SUMMARY

An object of the present invention is to provide a method for preparing (dimethylaminomethylene) malononitrile (I) by using a micro reaction system to overcome the drawbacks of the prior art. Compared to the prior methods, the method provided herein leads to significantly-improved yield and higher process efficiency in a remarkably shorter reaction time with simple operation, and the reaction and the liquid-liquid extraction processes are coupled and carried out continuously, and thus it is more suitable for industrial production. Moreover, it should be noted that it has not been reported on the use of a micro reaction system to continuously prepare (dimethylaminomethylene) malononitrile so far.

Technical solutions of the invention are specifically described as follows.

This application provides a method for preparing (dimethylaminomethylene) malononitrile using a micro reaction system, the micro reaction system comprising a micromixer and a microchannel reactor connected in series, and a centrifugal extraction unit consisting of a plurality of annular centrifugal extractors; the method including the following steps:

(1) mixing cyanoacetamide, N,N-dimethylformamide and a catalyst to produce a mixture; and pumping the mixture and phosphorus oxychloride into the micromixer at the same time to obtain a reaction mixture;

(2) allowing the reaction mixture outflowed from the micromixer to flow immediately into the microchannel reactor for continuous-flow reaction; and quenching the reaction with a quencher to produce a crude product after the reaction mixture flowed out of the microchannel reactor;

(3) adjusting the pH of the crude product to 2-10 with a pH regulator; and (4) pumping the crude product into the centrifugal extraction unit; introducing an organic solvent into the centrifugal extraction unit at the same time to perform continuous liquid-liquid extraction; collecting the organic phase outflowed from the centrifugal extraction unit to afford the target product (dimethylaminomethylene) malononitrile (I) after necessary workup.

The synthesis of (dimethylaminomethylene) malononitrile (I) provided herein is shown in the following scheme:

In some embodiments, in step (1), the catalyst is a pyridine compound, preferably pyridine, 2-picoline, 3-picoline, 4-picoline, 2,6-lutidine, 2,4-lutidine, 2,3-lutidine, 3,5-lutidine, 2,3,5-trimethylpyridine, 2,4,6-trimethylpyridine or a combination thereof, and more preferably pyridine, 2-picoline, 3-picoline, 4-picoline, 2,6-lutidine, or a combination thereof.

In some embodiments, in step (1), a molar ratio of cyanoacetamide to N,N-dimethylformamide to the catalyst to phosphorus oxychloride is 1: (1-10): (0.05-0.8): (1-10), preferably 1: (2-8): (0.07-0.5): (1.5-8).

In some embodiments, in step (2), the reaction in the microchannel reactor is performed at −40-100° C., preferably −20-50° C.

In some embodiments, in step (2), the reaction in the microchannel reactor is performed with a residence time of 0.2-60 min, preferably 2-40 min.

In some embodiments, in step (2), the backpressure in the microchannel reactor is 0.1-5 MPa, preferably 0.2-2 Mpa.

In some embodiments, in step (2), the quencher is ice water.

In some embodiments, in step (3), the pH regulator is an aqueous solution of an inorganic base.

In some embodiments, the inorganic base is an alkali metal carbonate, an alkali metal hydroxide or a combination thereof. Preferably, the inorganic base is lithium carbonate, sodium carbonate, potassium carbonate, lithium bicarbonate, sodium bicarbonate, potassium bicarbonate, lithium hydroxide, sodium hydroxide, potassium hydroxide, or a combination thereof.

In some embodiments, a mass percentage of the inorganic base in the aqueous solution is 20-95%, preferably 25-85%.

In some embodiments, in step (3), the pH of the crude product is adjusted to 3-9, preferably 6.5-7.2.

In some embodiments, in step (4), the organic solvent is a halogenated hydrocarbon, an acetate, a substituted benzene or an alkyl ether.

In some embodiments, the halogenated hydrocarbon is dichloromethane, chloroform, carbon tetrachloride, 1,2-dichloroethane or a combination thereof; the acetate is methyl acetate, ethyl acetate, isopropyl acetate, n-butyl acetate, tert-butyl acetate or a combination thereof the substituted benzene is toluene, xylene or a combination thereof; the alkyl ether is diethyl ether, propyl ether, methyl tert-butyl ether, diethylene glycol dimethyl ether, ethylene glycol butyl ether or a combination thereof.

In some embodiments, in step (4), the liquid-liquid extraction in the extraction unit is performed at 10-50° C. with a residence time of 0.1-10 min, preferably at 20-45° C. with a residence time of 0.15-5 min.

In some embodiments, the micromixer is a static mixer, a T-shaped micromixer, a Y-shaped micromixer, a coaxial flow micromixer or a flow-focusing micromixer.

In some embodiments, the microchannel reactor is a tubular microchannel reactor or a plate-type microchannel reactor.

In some embodiments, the microchannel reactor is a tubular microchannel reactor with an inner diameter of 100 μm-10 mm, preferably 120 μm-5.35 mm.

In some embodiments, the microchannel reactor is a plate-type microchannel reactor comprising a first heat exchange layer, a reaction layer and a second heat exchange layer sequentially arranged from top to bottom, wherein the reaction layer is provided with a reaction fluid channel, and a hydraulic diameter of the reaction fluid channel is 100 μm-10 mm, preferably 120 μm-5.35 mm.

In some embodiments, the micro reaction system further includes a vessel for pH adjustment, wherein an inlet of the vessel is connected to an outlet of the microchannel reactor; an outlet of the vessel is connected to an inlet of the centrifugal extraction unit; and the quenching in the step (2) and the pH adjustment in the step (3) are both performed in this vessel. In an embodiment, the quencher is placed in the vessel in advance, and when the reaction mixture outflowed from the microchannel reactor flows into this vessel, the reaction is quenched to obtain the crude product; after adjusted to pH 2-10 with a pH regulator, the crude product is pumped into the centrifugal extraction unit. In an embodiment, the quencher and the reaction mixture are simultaneously added into the vessel for quenching to obtain the crude product, and the pH of the crude product is adjusted to 2-10 and then pumped into the centrifugal extraction unit.

In some embodiments, the micro reaction system further comprises a vessel for pH adjustment; the micromixer comprises a first micromixer and a second micromixer; wherein an outlet of the first micromixer is connected to an inlet of the microchannel reactor; the second micromixer has a first inlet connected to an outlet of the microchannel reactor and a second inlet configured to allow the quencher to be pumped in; an outlet of the second micromixer is connected to an inlet of the vessel; an outlet of the vessel is connected to an inlet of the centrifugal extraction unit; and the quenching in step (2) is performed in the second micromixer, and the pH adjustment in step (3) is performed in the vessel.

In some embodiments, the first and second micromixers are independently a static mixer, a T-shaped micromixer, a Y-shaped micromixer, a coaxial flow micromixer or a flow-focusing micromixer; a first inlet of the second micromixer is connected to an outlet of the microchannel reactor. In an embodiment, the reaction mixture flows from the microchannel reactor into the second micromixer, meanwhile, the quencher is pumped into the second micromixer for quenching the reaction to obtain the crude product. The crude product then flows from the second micromixer to the vessel for pH adjustment.

In some embodiments, the micro reaction system further includes a pH meter and a computer. The pH meter includes a main body and at least one probe; the at least one probe is located inside the vessel, and the main body is connected with the at least one probe and the computer, respectively. The computer is also connected with a pump for pumping the pH regulator. The computer monitors a pH value of the crude product flowing into the vessel on line in real time through a software, and at the same time, the computer calculates and accurately controls a flow rate of the pH regulator pumped into the vessel in real time through the software, adjusting the pH of the crude product in the vessel to 2-10, preferably 3-9, and more preferably 6.5-7.2. Through the installation of the software, the computer can read the pH value measured by the pH meter in real time, and can also calculate and accurately adjust the flow rate of the pH regulator delivered by the pump in real time.

In some embodiments, the pH meter includes a plurality of probes, preferably 2-10 probes, which are connected with the main body of the pH meter, respectively.

In some embodiments, a buffer tank is provided between the vessel and the centrifugal extraction unit; an inlet of the buffer tank is connected to an outlet of the vessel, and an outlet of the buffer tank is connected to the inlet of centrifugal extraction unit. After undergoing pH adjustment, the crude product first enters the buffer tank from the vessel, and is then pumped into the centrifugal extraction unit.

In some embodiments, the centrifugal extraction unit comprises a plurality of annular centrifugal extractors, preferably 2-10 annular centrifugal extractors, connected in series.

In some embodiments, the capacity of the annular centrifugal extractor is 0.1-2 L.

Compared to the prior art, the present invention clearly highlights the following advantages.

The present invention performs catalytic dehydration condensation of cyanoacetamide, N,N-dimethylformamide and phosphorus oxychloride in a micro reaction system that includes a micromixer and a microchannel reactor to synthesize (dimethylaminomethylene) malononitrile (I). Since the micro reaction system has excellent mass and heat transfer and desirable intrinsic safety, the reaction can be carried out safely and quickly at room temperature, and can be completed within a few minutes with high yield (greater than 95%). Compared with prior methods, the method greatly lowers the reaction time and energy consumption, reduces the production of by-products, and significantly improves the yield of the product (dimethylaminomethylene) malononitrile (I). In addition, a plurality of annular centrifugal extractors connected in series are provided for continuous liquid-liquid extraction, which allows for desirable separation effect and high extraction efficiency (the separation yield approximates to the reaction yield). The reaction and the liquid-liquid extraction processes are coupled and conducted continuously, which maximizes the process efficiency and improves the product purity.

In the drawings: 1. first micromixer; 2. microchannel reactor; 3. vessel for pH adjustment; 4. first annular centrifugal extractor; 5. second annular centrifugal extractor; 6. thermostatic oil bath; 7. storage tank; 8. second micromixer; 9. computer; 10. pump; 11. pH meter; and 12. probe.

DETAILED DESCRIPTION OF EMBODIMENTS

The invention will be described in detail below with reference to the accompanying drawings and embodiments to make objects, technical solutions, and advantages of the invention clearer.

EXAMPLE 1

Figure 1:
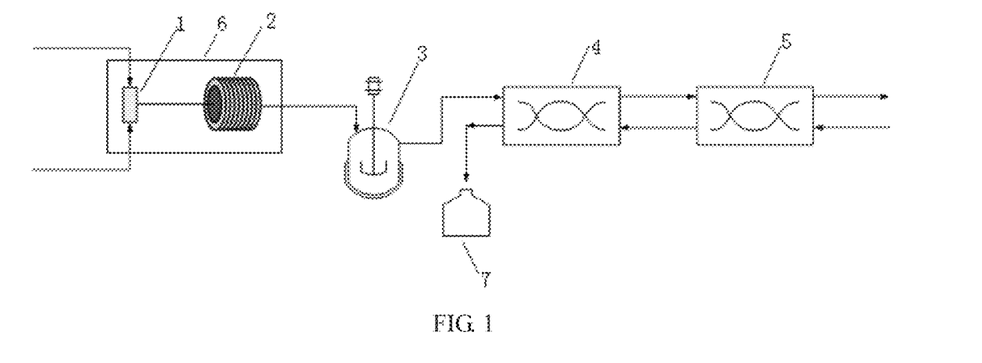
FIG. 1 is a schematic diagram of the structure of a micro reaction system in accordance with an embodiment of the present invention.

A method for preparing (dimethylaminomethylene) malononitrile by using a micro reaction system is provided in this example. As shown in FIG. 1, the micro reaction system includes a first micromixer 1, a microchannel reactor 2, a vessel 3 for pH adjustment, a first annular centrifugal extractor 4, and a second annular centrifugal extractor 5, and further includes a thermostatic oil bath 6 and a storage tank 7. The thermostatic oil bath 6 is used to adjust and control the reaction temperature in the microchannel reactor 2. The first micromixer 1 is a T-shaped micromixer. The microchannel reactor 2 is a polytetrafluoroethylene (PTFE) tubular microchannel reactor with an inner diameter of 0.8 mm and a reaction volume of 4 mL. The vessel 3, equipped with an agitation apparatus, is employed for pH adjustment. The storage tank 7 is used to collect the extract (i.e., organic phase) generated from the continuous liquid-liquid extraction process occurred consecutively in the first annular centrifugal extractor 4 and the second annular centrifugal extractor 5.

The method is specifically described as follows.

(1) 0.06 mol of cyanoacetamide, 0.18 mol of N,N-dimethylformamide and 0.006 mol of pyridine were mixed in a dry flask to obtain a mixture (density: 1.105 g/mL), and then the mixture and phosphorus oxychloride (25.08 g) were simultaneously pumped into the first micromixer 1 at a flow rate of 0.232 mL/min and 0.212 mL/min, respectively, and mixed therein, where a molar ratio of cyanoacetamide to N,N-dimethylformamide to pyridine to phosphorus oxychloride in the resultant reaction mixture was 1:3:0.1:2.726.

(2) The reaction mixture outflowed from the first micromixer 1 flowed immediately into the microchannel reactor 2 for continuous-flow reaction. The reaction in the microchannel reactor 2 was performed at 25° C. and 0.2 MPa (back-pressure) with a residence time of 9 min. The effluent from the microchannel reactor 2 was collected in the vessel 3, which contained ice water as the quencher, and hence the reaction was quenched to obtain the crude product.

(3) A 40% sodium hydroxide aqueous solution was added into the vessel 3 to adjust the pH of the crude product to 6.

(4) The crude product was then sequentially pumped into the first annular centrifugal extractor 4 and the second annular extractor 5 that were connected in series, and subjected to continuous countercurrent extraction with dichloromethane, where the crude product was pumped into the first annular centrifugal extractor 4 through its light phase inlet at a flow rate of 5 mL/min, and the dichloromethane was pumped into the second annular centrifugal extractor 5 through its heavy phase inlet at a flow rate of 5 mL/min; the rotation frequencies of the first annular centrifugal extractor 4 and the second annular centrifugal extractor 5 were both adjusted to 40 Hz; and the extractions in the first annular centrifugal extractor 4 and the second annular centrifugal extractor 5 were both performed at 25° C. with a residence time of 2 min; The resulting extract was collected in the storage tank 7, and then concentrated under reduced pressure to give an orange-red oil product (dimethylaminomethylene) malononitrile (I) in 98% purity (GC) with a yield of 95.8%, where the substrate cyanoacetamide achieved a 100% conversion.

EXAMPLE 2

A method for preparing (dimethylaminomethylene) malononitrile by using a micro reaction system is provided in this example, where the micro reaction system used herein is basically the same as that used in Example 1 except that only one annular centrifugal extractor (i.e., the first annular centrifugal 4) is used.

The method is specifically described as follows.

(1) 0.06 mol of cyanoacetamide, 0.18 mol of N,N-dimethylformamide, and 0.006 mol of pyridine were mixed in a dry flask to obtain a mixture (density 1.105 g/mL), and then the mixture and phosphorus oxychloride (25.08 g) were simultaneously pumped into the first micromixer 1 at a flow rate of 0.232 mL/min and 0.212 mL/min, respectively, and mixed therein, where a molar ratio of cyanoacetamide to N,N-dimethylformamide to pyridine to phosphorus oxychloride in the resultant reaction mixture was 1:3:0.1:2.726.

(2) The reaction mixture outflowed from the first micromixer 1 flowed immediately into the microchannel reactor 2 for continuous-flow reaction. The reaction in the microchannel reactor 2 was performed at 25° C. and 0.2 MPa (backpressure) with a residence time of 9 min. The effluent from the microchannel reactor 2 was collected in the vessel 3, which contained ice water as the quencher, and hence the reaction was quenched to obtain the crude product.

(3) A 40% sodium hydroxide aqueous solution was added into the vessel 3 to adjust the pH of the crude product to 6.

(4) The crude product was pumped into the first annular centrifugal extractor 4 through its light phase inlet at a flow rate of 5 mL/min, and at the same time dichloromethane was pumped into the first annular centrifugal extractor 4 through the heavy phase inlet at a flow rate of 5 mL/min. The rotation frequency of the first annular centrifugal extractor 4 was adjusted to 40 Hz, and the extraction in the first annular centrifugal extractor 4 was performed at 25° C. with a residence time of 2 min. The resulting extract was collected in the storage tank 7, and then concentrated under reduced pressure to give an orange-red oil product (dimethylaminomethylene) malononitrile (I) in 95.6% purity (GC) with a yield of 95.1%, where the substrate cyanoacetamide achieved a 100% conversion.

EXAMPLE 3

A method for preparing (dimethylaminomethylene) malononitrile by using a micro reaction system is provided in this example, where the method in this example is the same as that in Example 1; and the micro reaction system used herein is basically the same as that used in Example 1 except that the first micromixer 1 used herein is a Y-shaped micromixer.

The substrate cyanoacetamide achieved a 100% conversion, and the resulting product (dimethylaminomethylene) malononitrile was in 98.2% purity (GC) with a yield of 96.1%.

EXAMPLE 4

A method for preparing (dimethylaminomethylene) malononitrile by using a micro reaction system is provided in this example, where the method in this example is the same as that in Example 1; the micro reaction system used herein is basically the same as that used in Example 1 except that the first micromixer used herein 1 is a static micromixer.

The substrate cyanoacetamide achieved a 100% conversion, and the resulting product (dimethylaminomethylene) malononitrile was in 98.5% purity (GC) with a yield of 96.3%.

EXAMPLE 5

A method for preparing (dimethylaminomethylene) malononitrile by using a micro reaction system is provided in this example, where the method in this example is the same as that in Example 1; the micro reaction system used herein is basically the same as that used in Example 1 except that the first micromixer 1 used herein is a coaxial flow micromixer.

The substrate cyanoacetamide achieved a 100% conversion, and the resulting product (dimethylaminomethylene) malononitrile was in 98.2% purity (GC) with a yield of 96.2%.

EXAMPLE 6

A method for preparing (dimethylaminomethylene) malononitrile by using a micro reaction system is provided in this example, where the method in this example is the same as that in Example 1; the micro reaction system used herein is same as that used in Example 1 except that the first micromixer 1 used herein is a flow-focusing micromixer.

The substrate cyanoacetamide achieved a 100% conversion, and the resulting product (dimethylaminomethylene) malononitrile was in 98.4% purity (GC) with a yield of 96.3%.

EXAMPLE 7

A method for preparing (dimethylaminomethylene) malononitrile by using a micro reaction system is provided in this example. The micro reaction system used herein is the same as that used in Example 1; the method in this example is basically the same as that in Example 1 except that in the step (3), a 40% sodium hydroxide aqueous solution was added into the vessel 3 to adjust the pH of the crude product to 7.

The substrate cyanoacetamide achieved a 100% conversion, and the resulting product (dimethylaminomethylene) malononitrile was in 99.8% purity (GC) with a yield of 98.9%.

EXAMPLE 8

A method for preparing (dimethylaminomethylene) malononitrile by using a micro reaction system is provided in this example, where the micro reaction system used herein is the same as that used in Example 1; the method in this example is basically the same as that in Example 1 except that in the step (3), a 40% sodium hydroxide aqueous solution was added into the vessel 3 to adjust the pH of the crude product to 9.

The substrate cyanoacetamide achieved a 100% conversion, and the resulting product (dimethylaminomethylene) malononitrile was in 98.2% purity (GC) with a yield of 95.9%.

EXAMPLE 9

A method for preparing (dimethylaminomethylene) malononitrile by using a micro reaction system is provided in this example, where the micro reaction system used herein is the same as that used in Example 1; the method in this example is basically the same as that in Example 1 except that in the step (3), a 40% sodium hydroxide aqueous solution was added into the vessel 3 to adjust the pH of the crude product to 11.

The substrate cyanoacetamide achieved a 100% conversion, and the resulting product (dimethylaminomethylene) malononitrile was in 96.7% purity (GC) with a yield of 89%.

EXAMPLE 10

A method for preparing (dimethylaminomethylene) malononitrile by using a micro reaction system is provided in this example, where the micro reaction system used herein is the same as that used in Example 1; the method in this example is basically the same as that in Example 1 except that in the step (3), a 40% sodium hydroxide aqueous solution was added into the vessel 3 to adjust the pH of the crude product to 3.

The substrate cyanoacetamide achieved a 100% conversion, and the resulting product (dimethylaminomethylene) malononitrile was in 96.3% purity (GC) with a yield of 95%.

EXAMPLE 11

A method for preparing (dimethylaminomethylene) malononitrile by using a micro reaction system is provided in this example, where the micro reaction system used herein is the same as that used in Example 1; the method in this example is basically the same as that in Example 1 except that in the step (3), a 40% sodium hydroxide aqueous solution was added into the vessel 3 to adjust the pH of the crude product to 1.

The substrate cyanoacetamide achieved a 100% conversion, and the resulting product (dimethylaminomethylene) malononitrile was in 95.2% purity (GC) with a yield of 82%.

EXAMPLE 12

Figure 2:
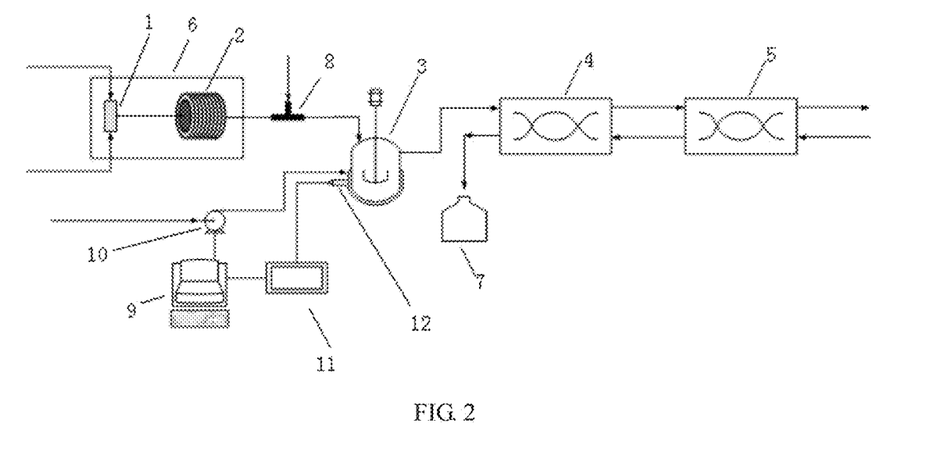
FIG. 2 is a schematic diagram of the structure of the micro reaction system in accordance with another embodiment of the present invention.

A method for preparing (dimethylaminomethylene) malononitrile by using a micro reaction system is provided in this example. As shown in FIG. 2, the micro reaction system includes a first micromixer 1, a microchannel reactor 2, a second micromixer 8, a vessel 3 for pH adjustment, a first annular centrifugal extractor 4, and a second annular centrifugal extractor 5, and further includes a thermostatic oil bath 6, a computer 9, a pump 10, a pH meter 11 and a storage tank 7. The thermostatic oil bath 6 is used to adjust and control the reaction temperature in the microchannel reactor 2. The pump 10 is used to pump a pH regulator into the vessel 3. The pH meter 11 includes a main body and a probe 12; the probe is 12 located inside the vessel 3, and the main body is connected with the probe 12 and the computer 9, respectively. The first micromixer 1 and the second micromixer 8 are both T-shaped micromixers. The microchannel reactor 2 is a PTFE tubular microchannel reactor with an inner diameter of 0.8 mm and a reaction volume of 4 mL. The vessel 3, equipped with an agitation apparatus, is employed for pH adjustment. A software is installed on the computer 9 that not only can read in the pH value measured by the pH meter 11 in real time, but also can calculate and accurately control the flow rate of the pump 10 (i.e., for pumping the pH regulator) in real time. The computer 9 monitors a pH value of the crude product in the vessel 3 in real time through the above-mentioned software, and at the same time, the computer 9 calculates and accurately controls the flow rate of the pH regulator pumping into the vessel 3 in real time through the software to adjust the pH of the crude product. The storage tank 7 is used to collect the extract (i.e., organic phase) generated from the continuous liquid-liquid extraction process occurred consecutively in annular centrifugal extractor 4 and annular centrifugal extractor 5.

The method is specifically described as follows.

(1) 0.06 mol of cyanoacetamide, 0.18 mol of N,N-dimethylformamide, and 0.006 mol of pyridine were mixed in a dry reaction flask to obtain a mixture (density: 1.105 g/mL), and then the mixture and phosphorus oxychloride (25.08 g) were pumped into the first micromixer 1 at a flow rate of 0.232 mL/min and 0.212 mL/min, respectively, and mixed therein, where a molar ratio of cyanoacetamide to N,N-dimethylformamide to pyridine to phosphorus oxychloride in the resultant reaction mixture was 1:3:0.1:2.726.

(2) The reaction mixture outflowed from the first micromixer 1 flowed immediately into the microchannel reactor 2 for continuous-flow reaction. The reaction in the microchannel reactor 2 was performed at 25° C. and 0.2 MPa (backpressure) with a residence time of 9 min. After that, the effluent from the microchannel reactor 2 was introduced into the second micromixer 8, and at the same time, ice water was pumped into the second micromixer 8 at a flow rate of 0.56 mL/min to quench the reaction to obtain a crude product.

(3) The crude product was then collected in the vessel 3, into which a 52% sodium hydroxide aqueous solution was pumped via the pump 10. In this process, the pH of the crude product was monitored by the computer 9 in real time, and it was accurately adjusted to 6 by controlling the flow rate of the sodium hydroxide aqueous solution through the software.

(4) The crude product was then sequentially pumped into the first annular centrifugal extractor 4 and the second annular extractor 5, and was subjected to continuous countercurrent extraction with dichloromethane, where the crude product was pumped into the first annular centrifugal extractor 4 through its light phase inlet at a flow rate of 5 mL/min, and dichloromethane was pumped into the second annular centrifugal extractor 5 through its heavy phase inlet at a flow rate of 5 mL/min; the rotation frequencies of the first annular centrifugal extractor 4 and the second annular centrifugal extractor 5 were both adjusted to 40 Hz; the extractions in the first annular centrifugal extractor 4 and the second annular centrifugal extractor 5 were both performed at 25° C. with a residence time of 2 min. The resulting extract was collected in the storage tank 7, and then concentrated under reduced pressure to give an orange-red oil product (dimethylaminomethylene) malononitrile (I) in 98% purity (GC) with a yield of 95.8%, where the reaction substrate cyanoacetamide achieved a 100% conversion.

EXAMPLE 13

A method for preparing (dimethylaminomethylene) malononitrile by using a micro reaction system is provided in this example, where the method in this example is the same as that in Example 12; the micro reaction system used herein is basically the same as that used in Example 12 except that the pH meter 11 includes a main body, a first probe and a second probe; the first probe and the second probe are located inside the vessel 3, and the main body is connected with the first and second probes and the computer 9, respectively.

The method is specifically described as follows.

(1) 0.06 mol of cyanoacetamide, 0.18 mol of N,N-dimethylformamide, and 0.006 mol of pyridine were mixed in a dry reaction flask to obtain a mixture (density: 1.105 g/mL), and then the mixture and phosphorus oxychloride (25.08 g) were simultaneously pumped into the first micromixer 1 at a flow rate of 0.232 mL/min and 0.212 mL/min, respectively, and mixed therein, where a molar ratio of cyanoacetamide to N,N-dimethylformamide to pyridine to phosphorus oxychloride in the resultant reaction mixture was 1:3:0.1:2.726.

(2) The reaction mixture outflowed from the first micromixer 1 flowed immediately into the microchannel reactor 2, and the reaction was performed at 25° C. and 0.2 MPa (backpressure) with a residence time of 9 min. After that, the effluent from the microchannel reactor 2 was introduced into the second micromixer 8, and at the same time, the ice water was pumped into the second micromixer 8 at a flow rate of 0.56 mL/min to quench the reaction to obtain a crude product.

(3) The crude product was then collected in the vessel 3, into which a 52% sodium hydroxide aqueous solution was pumped via the pump 10. In this process, the pH of the crude product was monitored by the computer 9 in real time, and it was accurately adjusted to 6 by controlling the flow rate of the sodium hydroxide aqueous solution through the software.

(4) The crude product was sequentially pumped into the first annular centrifugal extractor 4 and the second annular extractor 5, and was subjected to continuous countercurrent extraction with dichloromethane, where the crude product was pumped into the first annular centrifugal extractor 4 through its light phase inlet at a flow rate of 5 mL/min, and the dichloromethane was pumped into the second annular centrifugal extractor 5 through its heavy phase inlet at a flow rate of 5 mL/min; the rotation frequencies of the first annular centrifugal extractor 4 and the second annular centrifugal extractor 5 were both adjusted to 40 Hz; the extractions in the first annular centrifugal extractor 4 and the second annular centrifugal extractor 5 were both performed at 25° C. with a residence time of 2 min. The resulting extract was collected in the storage tank 7, and then concentrated under reduced pressure to give an orange-red oil product (dimethylaminomethylene) malononitrile (I) in 98.9% purity (GC) with a yield of 96.8%, where the substrate cyanoacetamide achieved a 100% conversion.

EXAMPLE 14

A method for preparing (dimethylaminomethylene) malononitrile by using a micro reaction system is provided in this example, where the micro reaction system used herein is basically the same as that used in Example 12 except that the microchannel reactor 2 used herein is a stainless-steel tubular microchannel reactor with an inner diameter of 0.6 mm and a reaction volume of 5 mL.

The method is specifically described as follows.

(1) 0.06 mol of cyanoacetamide, 0.18 mol of N,N-dimethylformamide, and 0.006 mol of pyridine were mixed in a dry flask to obtain a mixture (density: 1.105 g/mL), and then the mixture and phosphorus oxychloride (25.07 g) were simultaneously pumped into the first micromixer 1 at a flow rate of 0.261 mL/min and a flow rate of 0.238 mL/min, respectively, and mixed therein, where a ratio of cyanoacetamide to N,N-dimethylformamide to pyridine to phosphorus oxychloride in the resultant reaction mixture was 1:3:0.1:2.725.

(2) The reaction mixture outflowed from the first micromixer 1 flowed immediately into the microchannel reactor 2, and the reaction was performed at 27° C. and 0.3 MPa (backpressure) with a residence time of 10 min. The effluent from the microchannel reactor 2 was introduced into the second micromixer 8, and at the same time, the ice water was pumped into the second micromixer 8 at a flow rate of 0.63 mL/min to quench the reaction to obtain a crude product.

(3) The crude product was then collected in the vessel 3, into which a 50% potassium hydroxide aqueous solution was pumped via the pump 10. In this process, the pH of the crude product was monitored by the computer 9 in real time, and it was accurately adjusted to 6.5 by controlling the flow rate of the sodium hydroxide aqueous solution through the software.

(4) The crude product was sequentially pumped into the first annular centrifugal extractor 4 and the second annular extractor 5, and was subjected to continuous countercurrent extraction with ethyl acetate, where the crude product was pumped into the first annular centrifugal extractor 4 through its light phase inlet at a flow rate of 5.56 mL/min, and the ethyl acetate was pumped into the second annular centrifugal extractor 5 through its heavy phase inlet at a flow rate of 5.56 mL/min; the rotation frequencies of the first annular centrifugal extractor 4 and the second annular centrifugal extractor 5 were both adjusted to 40 Hz; the extractions in the first annular centrifugal extractor 4 and the second annular centrifugal extractor 5 were both performed at 25° C. with a residence time of 1.8 min; The resulting extract was collected in the storage tank 7, and then concentrated under reduced pressure to give an orange-red oil product (dimethylaminomethylene) malononitrile (I) in 99.7% purity (GC) with a yield of 98.7%, where the substrate cyanoacetamide achieved a 100% conversion.

EXAMPLE 15

A method for preparing (dimethylaminomethylene) malononitrile by using a micro reaction system is provided in this example, where the micro reaction system used herein is basically the same as that used in Example 12 except that the microchannel reactor 2 used herein is a stainless-steel tubular microchannel reactor with an inner diameter of 0.5 mm and a reaction volume of 8 mL.

The method is specifically described as follows.

(1) 0.06 mol of cyanoacetamide, 0.18 mol of N,N-dimethylformamide, and 0.006 mol of pyridine were mixed in a dry flask to obtain a mixture (density: 1.105 g/mL), and then the mixture and phosphorus oxychloride (25 g) were simultaneously pumped into the first micromixer 1 at a flow rate of 0.627 mL/min and 0.57 mL/min, respectively, and mixed therein, where a molar ratio of cyanoacetamide to N,N-dimethylformamide to pyridine to phosphorus oxychloride in the resultant reaction mixture was 1:3:0.1:2.718.

(2) The reaction mixture outflowed from the first micromixer 1 flowed immediately into the microchannel reactor 2 for continuous-flow reaction, and the reaction was performed at 23° C. and 0.5 MPa (backpressure) with a residence time of 6.7 min. The effluent from the microchannel reactor 2 was introduced into the second micromixer 8, into which the ice water was pumped at a flow rate of 1.5 mL/min to quench the reaction to obtain a crude product.

(3) The crude product was then collected in the vessel 3, into which a 40% potassium hydroxide aqueous solution was pumped via the pump 10. In this process, the pH of the crude product was monitored by the computer 9 in real time, and it was accurately adjusted to 6.8 by controlling the flow rate of the potassium hydroxide aqueous solution through the software.

(4) The crude product was sequentially pumped into the first annular centrifugal extractor 4 and the second annular extractor 5, and was subjected to continuous countercurrent extraction with 1,2-dichloroethane, where the crude product was pumped into the first annular centrifugal extractor 4 through a light phase inlet at a flow rate of 7.14 mL/min, and the 1,2-dichloroethane was pumped into the second annular centrifugal extractor 5 through a heavy phase inlet at a flow rate of 7.14 mL/min; the rotation frequencies of the first annular centrifugal extractor 4 and the second annular centrifugal extractor 5 were both adjusted to 40 Hz; the extractions in the first annular centrifugal extractor 4 and the second annular centrifugal extractor 5 were both performed at 25° C. with a residence time of 1.4 min. The resulting extract was collected in the storage tank 7, and then concentrated under reduced pressure to give an orange-red oil product (dimethylaminomethylene) malononitrile (I) in 99.8% purity (GC) with a yield of 98.5%, where the substrate cyanoacetamide achieved a 100% conversion.

EXAMPLE 16

A method for preparing (dimethylaminomethylene) malononitrile by using a micro reaction system is provided in this example, where the micro reaction system used herein is basically the same as that used in Example 12 except that the microchannel reactor 2 used herein is a plate-type microchannel reactor with a length of 12 cm, a width of 10 cm, and a height of 3 cm. The plate-type microchannel reactor includes, in sequence from top to bottom, a first temperature-control medium layer, a reaction layer, and a second temperature-control medium layer; the first temperature-control medium layer and the second temperature-control medium layer are used to adjust and control the temperature of the reaction layer, and the reaction layer is provided with a reaction fluid channel; a cross section of the reaction fluid channel has a size of 400 µm (width)×600 µm (length); a hydraulic diameter of the reaction fluid channel is 480 µm; and the volume of the reaction fluid channel is 8 mL.

The method is specifically described as follows.

(1) 0.06 mol of cyanoacetamide, 0.18 mol of N,N-dimethylformamide, and 0.006 mol of pyridine were mixed in a dry reaction flask to obtain a mixture (density: 1.105 g/mL), and then the mixture and phosphorus oxychloride (21.05 g) were simultaneously pumped into the first micromixer 1 a flow rate of 0.627 mL/min and 0.48 mL/min, respectively, and mixed therein, where a molar ratio of cyanoacetamide to N,N-dimethylformamide to pyridine to phosphorus oxychloride in the resultant reaction mixture was 1:3:0.1:2.288.

(2) The reaction mixture outflowed from the first micromixer 1 flowed immediately into the microchannel reactor 2, and the reaction was performed at 25° C. and 0.8 MPa (backpressure) with a residence time of 7.2 min. Then the effluent from the microchannel reactor 2 was introduced into the second micromixer 8, into which the ice water was pumped at a flow rate of 1.44 mL/min to quench the reaction to obtain a crude product.

(3) The crude product was then collected in the vessel 3, into which a 40% sodium hydroxide aqueous solution was pumped via the pump 10. In this process, the pH of the crude product was monitored by the computer 9 in real time, and it was accurately adjusted to 7.2 by controlling the flow rate of the sodium hydroxide aqueous solution through the software.

(4) The crude product was sequentially pumped into the first annular centrifugal extractor 4 and the second annular extractor 5, and subjected to continuous extraction with methyl tert-butyl ether, where the crude product was pumped into the first annular centrifugal extractor 4 through a light phase inlet at a flow rate of 6.67 mL/min, and the methyl tert-butyl ether was pumped into the second annular centrifugal extractor 5 through a heavy phase inlet at a flow rate of 6.67 mL/min; the rotation frequencies of the first annular centrifugal extractor 4 and the second annular centrifugal extractor 5 were both adjusted to 40 Hz; the extractions in the first annular centrifugal extractor 4 and the second annular centrifugal extractor 5 were both performed at 25° C. with a residence time of 1.5 min. The resulting extract was collected in the storage tank 7, and then concentrated under reduced pressure to give an orange-red oil product (dimethylaminomethylene) malononitrile (I) in 99.2% purity (GC) with a yield of 98.1%, where the substrate cyanoacetamide achieved a 100% conversion.

EXAMPLE 17

A method for preparing (dimethylaminomethylene) malononitrile by using a micro reaction system is provided in this example, where the micro reaction system used herein is basically the same as that used in Example 12 except that the microchannel reactor 2 is a plate-type microchannel reactor with a length of 12 cm, a width of 10 cm, and a height of 3 cm. The plate-type microchannel reactor includes, in sequence from top to bottom, a first temperature-control medium layer, a reaction layer, and a second temperature-control medium layer; the first temperature-control medium layer and the second temperature-control medium layer are used to adjust and control the temperature of the reaction layer, and the reaction layer is provided with a reaction fluid channel; the cross section of the reaction fluid channel has a size of 550 µm (width)×550 µm (length); a hydraulic diameter of the reaction fluid channel is 550 µm; and the volume of the reaction fluid channel is 8.4 mL.

The method is specifically described as follows.

(1) 0.06 mol of cyanoacetamide, 0.18 mol of N,N-dimethylformamide, and 0.006 mol of pyridine were mixed in a dry flask to obtain a mixture (density 1.105 g/mL), and then the mixture and phosphorus oxychloride (75.24 g) were simultaneously pumped into the first micromixer 1 at a flow rate of 0.549 mL/min and 0.5 mL/min, respectively, and mixed therein, where a molar ratio of cyanoacetamide to N,N-dimethylformamide to pyridine to phosphorus oxychloride in the resultant reaction mixture was 1:3:0.1:2.726.

(2) The reaction mixture outflowed from the first micromixer 1 flowed immediately into the microchannel reactor 2, and the reaction was performed in the microchannel reactor 2 at 25° C. and 1.0 MPa (backpressure) with a residence time of 8 min. The effluent from the microchannel reactor 2 was introduced into the second micromixer 8, into which the ice water was pumped at a flow rate of 1.35 mL/min to quench the reaction to obtain a crude product.

(3) The crude product was then collected in the vessel 3, into which a 50% sodium hydroxide aqueous solution was pumped via the pump 10, where the pH of the crude product was monitored by the computer 9 in real time, and it was accurately adjusted to 6.3 by controlling the flow rate of the sodium hydroxide aqueous solution through the software.

(4) The crude product was sequentially pumped into the first annular centrifugal extractor 4 and the second annular extractor 5, and subjected to continuous extraction with methyl tert-butyl ether, where the crude product was pumped into the first annular centrifugal extractor 4 through a light phase inlet at a flow rate of 7.7 mL/min, and the methyl tert-butyl ether was pumped into the second annular centrifugal extractor 5 through a heavy phase inlet at a flow rate of 7.7 mL/min; the rotation frequencies of the first annular centrifugal extractor 4 and the second annular centrifugal extractor 5 were both adjusted to 40 Hz; the extractions in the first annular centrifugal extractor 4 and the second annular centrifugal extractor 5 were both performed at 25° C. with a residence time of 1.3 min. The resulting extract was collected in the storage tank 7, and then concentrated under reduced pressure to give an orange-red oil product (dimethylaminomethylene) malononitrile (I) in 98.6% purity (GC) with a yield of 96.5%, where the substrate cyanoacetamide achieved a 100% conversion.

COMPARATIVE EXAMPLE 1

In this example, a method for preparing (dimethylaminomethylene) malononitrile by using a batch stirred reactor is provided, where the batch stirred reactor is a 150 mL round-bottom flask.

Specifically, 0.06 mol of cyanoacetamide, 0.18 mol of N,N-dimethylformamide and 0.006 mol of pyridine were mixed in the dry round-bottom flask, in which the temperature was adjusted to −10° C. 25.07 g of phosphorus oxychloride was dropwise added within 2 h. The reaction was conducted at −10° C. under agitation. During the reaction process, the reaction mixture was sampled and analyzed regularly, where the substrate cyanoacetamide achieved a conversion of about 48% after 3 h, about 67% after 6 h, about 82% after 9 h, and about 97% after 12 h. After the reaction was completed, the product (dimethylaminomethylene) malononitrile (I) achieved a yield of 77% (GC), and the resulting crude product was poured into 150 mL of ice water, into which a 50% potassium hydroxide aqueous solution was added to adjust the pH of the crude product to 6.5. Then the crude product was extracted with ethyl acetate for 3 times (3×300 mL). The organic phases were combined and concentrated under reduced pressure to give an orange-red oil product (dimethylaminomethylene) malononitrile in 96.8% purity (GC) with a yield of 66%. The reaction and workup took about 15 h in total. Due to the reaction is intense exothermic in nature, the batch-wise reaction was required to be carried out at a low temperature to ensure safety, and thus the reaction temperature was controlled at −10° C. The low-temperature conditions required a low-temperature thermostatic bath, which caused additional energy consumption.

COMPARATIVE EXAMPLE 2

In this example, a method for preparing (dimethylaminomethylene) malononitrile by using a batch stirred reactor is provided, where the batch stirred reactor is a 500 mL round-bottom flask.

Specifically, 0.18 mol of cyanoacetamide, 0.54 mol of N,N-dimethylformamide, and 0.018 mol of pyridine were mixed in the dry round-bottom flask, in which the temperature was adjusted to −10° C. 75.24 g of phosphorus oxychloride was dropwise added within 4 h. The reaction was performed at −10° C. under agitation. During the reaction process, the reaction mixture was sampled and analyzed regularly, where the substrate cyanoacetamide achieved a conversion of about 32% after 3 h, about 51% after 6 h, about 68% after 9 h, about 79% after 12 h, about 88% after 15 h, and about 96.7% after 18 h. After the reaction was completed, the product (dimethylaminomethylene) malononitrile (I) achieved a yield of 72% (GC), and the crude product was poured into 500 mL of ice water, into which a 50% sodium hydroxide aqueous solution was added to adjust the pH of the crude product to 6.3. Then the crude product was extracted with methyl tert-butyl ether for 3 times (3×300 mL). The organic phases were combined and concentrated under reduced pressure to give an orange-red oil product (dimethylaminomethylene) malononitrile in 97.1% purity (GC) with a yield of 70%. The reaction and workup took about 24 h in total. Due to the reaction is intense exothermic in nature, the batch-wise reaction was required to be carried out at a low temperature to ensure safety, and thus the reaction temperature was controlled at −10° C. The low-temperature conditions required a low-temperature thermostatic bath, which caused additional energy consumption.

The Comparative Example 1 was the same as Example 14 in the molar ratio of reactants, and the Comparative Example 2 and Example 17 had the same molar ratio of reactants. Compared to the batch stirred reactor, the micro reaction system used herein can achieve the continuous synthesis of the target product (dimethylaminomethylene) malononitrile, and the reaction can be completed within a few minutes, which considerably shortened the reaction time. Furthermore, the reaction can be performed safely at room temperature in the micro reaction system, and it was not necessary to employ low temperature reaction conditions, thus greatly reducing the energy consumption. The reaction and the liquid-liquid extraction processes were coupled and carried out continuously, so that the overall process efficiency was maximized. The isolated yield from the present invention was close to the reaction yield (more than 95%), and high purity product was obtained.

It should be noted that the above-mentioned embodiments are only illustrative of the technical solutions of the present invention, and are not intended to limit the invention. It should be noted that any modification, replacement and change made by those skilled in the art without deviating from the spirit of the invention should fall within the scope of the invention.

What is claimed is:

1. A method for preparing (dimethylaminomethylene) malononitrile using a micro reaction system, the micro reaction system comprising a micromixer and a microchannel reactor connected in series, and a centrifugal extraction unit consisting of a plurality of annular centrifugal extractors; the method comprising:
    (1) mixing cyanoacetamide, N,N-dimethylformamide and a catalyst to produce a mixture; and pumping the mixture and phosphorus oxychloride into the micromixer at the same time to obtain a reaction mixture;
    (2) allowing the reaction mixture outflowed from the micromixer to flow immediately into the microchannel reactor for continuous-flow reaction; and quenching the reaction with a quencher to produce a crude product after the reaction mixture flowed out of the microchannel reactor;
    (3) adjusting the pH of the crude product to 2-10 with a pH regulator; and
    (4) pumping the crude product into the centrifugal extraction unit; introducing an organic solvent into the centrifugal extraction unit at the same time to perform continuous liquid-liquid extraction; collecting the organic phase outflowed from the centrifugal extraction unit to afford the target product (dimethylaminomethylene) malononitrile (I) after necessary workup.

2. The method of claim 1, wherein in step (1), the catalyst is a pyridine compound.

3. The method of claim 1, wherein in step (1), a molar ratio of cyanoacetamide to N,N-dimethylformamide to the catalyst to phosphorus oxychloride is 1:(1-10): (0.05-0.8): (1-10).

4. The method of claim 1, wherein in step (2), the reaction in the microchannel reactor is performed at −40-100° C. with a residence time of 0.2-60 min.

5. The method of claim 1, wherein in step (2), the quencher is ice water.

6. The method of claim 1, wherein in step (3), the pH regulator is an aqueous solution of an inorganic base.

7. The method of claim 1, wherein in step (3), the pH of the crude product is adjusted to 3-9.

8. The method of claim 1, wherein in step (4), the organic solvent is a halogenated hydrocarbon, an acetate, a substituted benzene or an alkyl ether.

9. The method of claim 1, wherein in step (4), the liquid-liquid extraction in the annular centrifugal extractor is performed at 10-50° C. with a residence time of 0.1-10 min.

10. The method of claim 1, wherein the micromixer is a static mixer, a T-shaped micromixer, a Y-shaped micromixer, a coaxial flow micromixer or a flow-focusing micromixer.

11. The method of claim 1, wherein the microchannel reactor is a tubular microchannel reactor or a plate-type microchannel reactor.

12. The method of claim 11, wherein the microchannel reactor is a tubular microchannel reactor having an inner diameter of 100 μm-10 mm.

13. The method of claim 11, wherein the microchannel reactor is a plate-type microchannel reactor comprising: a first heat exchange layer, a reaction layer, and a second heat exchange layer sequentially arranged from top to bottom; wherein the reaction layer is provided with a reaction fluid channel, and the hydraulic diameter of the reaction fluid channel is 100 μm-10 mm.

14. The method of claim 1, wherein the micro reaction system further comprises:
a vessel for pH adjustment;
wherein an inlet of the vessel is connected to an outlet of the microchannel reactor; an outlet of the vessel is connected to an inlet of the centrifugal extraction unit; and the quenching in step (2) and the pH adjustment in step (3) are both performed in the vessel.

15. The method of claim 1, wherein the micro reaction system further comprises:
a vessel for pH adjustment;
wherein the micromixer comprises a first micromixer and a second micromixer; wherein an outlet of the first micromixer is connected to an inlet of the microchannel reactor; the second micromixer has a first inlet connected to an outlet of the microchannel reactor and a second inlet configured to allow the quencher to be pumped in; an outlet of the second micromixer is connected to an inlet of the vessel; an outlet of the vessel is connected to an inlet of the centrifugal extraction unit; and the quenching in step (2) is performed in the second micromixer, and the pH adjustment in step (3) is performed in the vessel.

16. The method of claim 15, wherein the first and second micromixers are independently a static mixer, a T-shaped micromixer, a Y-shaped micromixer, a coaxial flow micromixer or a flow-focusing micromixer.

17. The method of claim 15, wherein the micro reaction system further comprises:
a pH meter and a computer;
wherein the pH meter comprises a main body and at least one probe; the at least one probe is located inside the vessel, and the main body is connected with the at least one probe and the computer, respectively; the computer is also connected with a pump for pumping the pH regulator; the computer monitors the pH value of the crude product flowing into the vessel on line in real time through a software, and at the same time, the computer calculates and controls the flow rate of the pH regulator pumped into the vessel in real time through the software to adjust the pH of the crude product in the vessel to 3-9.

18. The method of claim 17, wherein the pH meter comprises a plurality of probes, and the probes are connected with the main body of the pH meter at the same time.

19. The method of claim 14, wherein a buffer tank is provided between the vessel and the centrifugal extraction unit; an inlet of the buffer tank is connected to the outlet of the vessel, and an outlet of the buffer tank is connected to the inlet of the centrifugal extraction unit; after undergoing pH adjustment and entering the buffer tank from the vessel, the crude product is pumped into the centrifugal extraction unit.

20. The method of claim 1, wherein the centrifugal extraction unit comprises a plurality of annular centrifugal extractors connected in series.

* * * * *